United States Patent [19]

Laure

[11] 4,134,158
[45] Jan. 16, 1979

[54] KNEE JOINT PROSTHESIS

[75] Inventor: George R. Laure, Kalamazoo, Mich.

[73] Assignee: Laure Prosthetics, Inc., Portage, Mich.

[21] Appl. No.: 826,896

[22] Filed: Aug. 22, 1977

[51] Int. Cl.² .............................................. A61F 1/24
[52] U.S. Cl. ................................... 3/1.911; 128/92 C
[58] Field of Search .................................. 3/1.9–1.911; 128/92 C

[56] References Cited

U.S. PATENT DOCUMENTS

| | | | |
|---|---|---|---|
| 3,638,243 | 2/1972 | Campbell, Jr. et al. | 3/1.91 |
| 3,694,821 | 10/1972 | Moritz | 3/1.911 |
| 3,918,101 | 11/1975 | Lagrange et al. | 3/1.911 |
| 3,945,053 | 3/1976 | Hillberry et al. | 3/1.911 |
| 3,990,118 | 11/1976 | Strickland et al. | 3/1.91 |

Primary Examiner—Ronald L. Frinks

Attorney, Agent, or Firm—Blanchard, Flynn, Thiel, Boutell & Tanis

[57] ABSTRACT

Prosthetic knee joint. A prosthetic knee joint is proposed which incorporates into a single product a variety of previously recognized desirable features. The joint in question has a generally cylindrically shaped knob on one component thereof and a receptacle for receiving said knob in the other component thereof. Said receptacle is designed for full engagement of said cylindrical knob less only the clearance required to permit the desired pivotal motion of said joint and the components defining said receptacle are arranged so that only shear stress is normally imposed on the screws by which the components defining said receptacle are assembled and the parts are further arranged in order that wide contact surfaces between the components of said prosthesis are provided for direct transmission of load between said components without a major portion thereof being transmitted through said joint.

5 Claims, 4 Drawing Figures

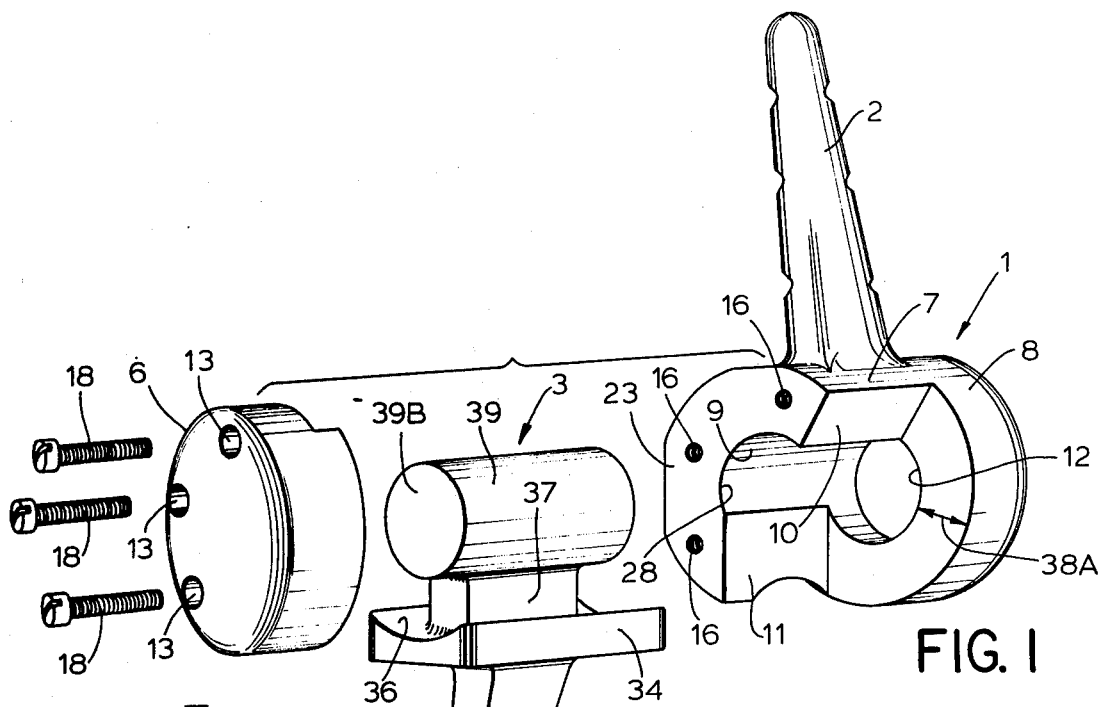
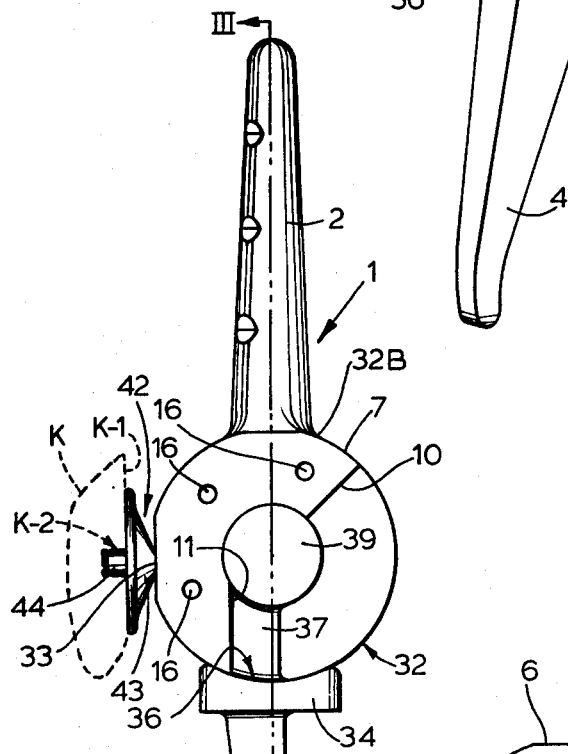
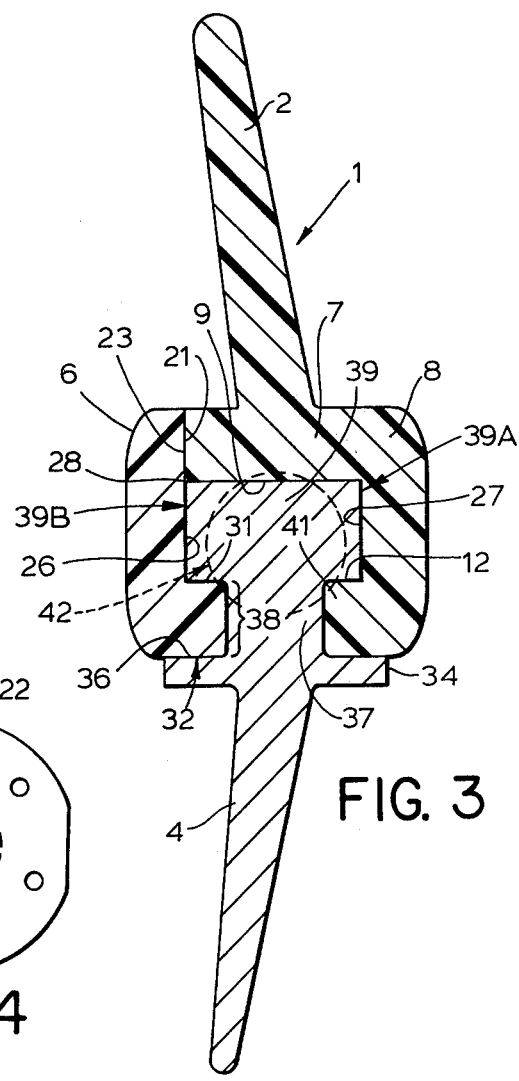
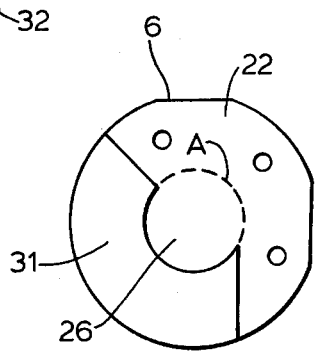
FIG. 1
FIG. 2
FIG. 3
FIG. 4

KNEE JOINT PROSTHESIS

FIELD OF THE INVENTION

The invention relates to a knee joint prosthesis and particularly to a type thereof having two components with a knob and cavity relationship therebetween wherein relatively wide contact surfaces are provided for direct transmission of load from one component to the other and wherein the screws fastening together the parts defining the cavity are normally subjected only to shear stress.

BACKGROUND OF THE INVENTION

In the recent accelerating activity with respect to metal, plastics, and composite prostheses for various joints in the human body, a great deal of attention has been paid to the knee joint. As is well known, this joint must absorb substantial stress, primarily loadings directed axially of the adjacent leg portions, but also some flexing stresses. In fact, the vertical loading on the knee joint of a 200-pound man often reaches values as high as at least 800 pounds per square inch.

There have in the past been designed a number of prosthetic knee joints intended for manufacture from plastics materials, or from plastics and metal materials, wherein large surfaces have been provided as bearing surfaces for the support of these loads and to reduce the unit stress thereon and these designs have had many good features. However, as for example in the patent to Lagrange, U.S. Pat. No. 3,918,101, wherein this basic concept is developed, there is also provided a centrally split housing to define the joint cavity. In this case, the two parts of such housing are held together by screws and hence in conditions of use involving tension through the joint such screws will be subjected to tension forces. Since these forces must be resisted by the thread screws in the plastics material, this presents a point of weakness.

In other proposals, such as Goldberg U.S. Pat. No. 3,765,033, wherein the broad concept of providing wide support for the joint loading is suggested, the components are fastened together by a transversely positioned pin in an oversize bore. This not only requires quite precise original dimensioning but also inevitably provides for looseness in the joint, particularly when the user's leg is under tension and it would be unsatisfactory.

Various other disclosures recognize the problem and attempt to solve it by providing wide support surfaces as above mentioned but they all have other features involving either looseness, undesirable concentration of forces in certain use situations with resulting points of weakness or other undesirable constructional and/or operational features.

Accordingly, the objects of the invention include:

1. To provide a prosthetic knee joint which can be formed from plastics materials and/or plastics-metal materials as desired, which will provide heavy load capabilities in the normal condition of use as in walking by the user, but which will provide firm and smooth bending of the knee under all circumstances of use and permit no looseness therein even under conditions of lateral flexure or leg tension.

2. To provide a prosthesis, as above mentioned, wherein the load in all directions of major magnitudes is at least partially carried by a solid piece of material and wherein the rest of such load is carried by shear stress on the screws holding component parts together, and only very minor loadings will apply tension stress to such screws.

3. To provide a prosthesis, as above mentioned, wherein the joint will be firm and solid and wherein particularly there will be no free play present.

4. To provide a prosthesis, as aforesaid, which will be of sufficiently simple construction as to be formable in relatively large masses by molding and will be free from complex parts and consequent difficulties in molding.

Other objects and purposes will be apparent to persons acquainted with devices of this general type upon reading the following specification and inspection of the accompanying drawings.

BRIEF DESCRIPTION OF THE DRAWINGS

In the drawings:

FIG. 1 is an oblique exploded view of an embodiment of the invention.

FIG. 2 is an end view of the socket and cylinder portions in assembled relationship taken from the left end as appearing in FIG. 1.

FIG. 3 is a central section taken on the line III—III of FIG. 2 with, however, the cap portion in place.

FIG. 4 is an elevation view of the cap taken from the righthand end as appearing in FIG. 1.

DETAILED DESCRIPTION

Turning now to the drawings in more detail, there is shown a recess portion 1 having a conventional prong 2 thereon for insertion into the femur, a cylinder portion 3 having a prong 4 thereon for insertion into the user's tibia and a cap portion 6 for closing the end of the cavity provided within the recess portion 1.

Said recess portion 1 comprises a central zone 7 and an end portion 8. Said central zone 7 is of generally cylindrical shape with a portion of such cylinder removed to provide a concentric, substantially hemicylindrical, recess 9, a surface 10 extending radially from the exterior of said cylindrical body 7 to the hemispherical surface defining the recess 9 and a further surface 11 extending from another portion on the exterior surface of said cylindrical body 7 to the surface defining the hemispherical recess 9 and intersecting therewith. The surface 11 is, as best seen in FIG. 2, substantially parallel with the center line of the prong 2 and positioned on the side of the recess 9 remote from both said prong 2 and said surface 10. The surface 10 defines an angle with respect to said center line and is angularly spaced from said surface 11 an angular distance dependent upon the number of degrees of flexure desired for the prosthesis, here approximately 120°.

The end portion 8 comprises in its outer surface a substantial continuation of the correspondingly adjacent portions of the central section 7 and is provided internally with a blind cylindrical opening 12, a part of whose walls are a continuation of the wall defining the hemispherical recess 9.

The end cap 6 forms with the central section 7 a mirror image of the end portion 8 and is fastened thereto by a convenient means such as suitable screws 18 positioned in the screw holes 13. Said screw holes are in register when the parts are assembled with threaded openings 16 by which screws 18 may be utilized to hold the parts together.

The inner surface 21 of the end cap 6 is flat throughout an arcuate portion 22 thereof, said portion being that portion which bears against the end surface 23 of said central portion 7. A further portion of said end cap 6 comprises a circular zone 26 which is concentric with and opposed to the end 27 of the blind opening 12, the broken line A indicating that portion of the boundary of the area 26 which lies against the edge 28 of the hemispherical surface 9. Said surfaces 21 and 26 are perpendicular to the axis of the recess 9 and blind opening 12. A projecting portion 31 extends centrally past the surface 23 whereby to define in effect when the parts are assembled a blind opening between the central part 7 and the part 6 corresponding to and identical (in mirror image) with the blind opening 12.

Upon reference to FIGS. 2 and 4, it will be seen that the lower surface of the socket part 1, including the central portion 7, the end portion 8 and the cap 6 all cooperate to define an arcuate cylindrical external surface 32 which is concentric with the center of the hemispherical recess 9. A flat portion 33 may be provided if desired for use in affixing a knee cap thereto but at least that portion of said surface 32 contacted by the cylinder part 3 of the prosthesis between its extreme pivoted positions, namely between the positions 32A and 32B of the socket part 1, are arcuate as above stated for reasons appearing below.

Turning now to cylinder part 3, there is provided as above mentioned the prong 4 for reception into the tibia of the user. At the upper end of said prong is positioned a platform 34 whose upper surface 36 is arcuate on the same radius as the surface 32. Projecting further upwardly in a substantial continuation of the prong 4 is a neck 37 which is of length substantially equal to (or a clearance distance greater than) the dimension 38 of the cap 6 and the equal dimension 38A of the flange 41 of the end portion 8. At the upper end of the neck 37 is a cylindrical head 39 which is of diameter and length to fit snugly into the blind opening 12, against the hemicylindrical surface of the recess 9 and into the blind opening formed between the central portion 7 and the end cap 6 when said two portions are assembled as shown in FIG. 3.

A slide unit 42 is shown for positioning between, and cooperation with, both the normal knee cap K (which usually does not need replacing) and the joint prosthesis of the invention. Same is shaved by the surgeon to present the flat surface K1 on the side facing the joint and the small pilot hole K2 drilled centrally therein. Said slide 42 has a contact portion 43 and a locating pin 44. The locating pin is received into the pilot opening K2 and the contact portion 43 is then positioned to bear against the flat 33 of the prosthesis. As the knee flexes, said contact portion will ride as needed on the outer (leftward as appearing in FIG. 2) surface of the recess portion 1. The muscles and tendons normally attached to the natural knee cap will in most instances remain attached thereto and will continue after the prosthesis is installed to operate in a normal manner with the muscles and tendons controlling the prosthetic knee joint.

Since the parts are large and provided with simple planar or arcuately cylindrical surfaces, same can be and are molded to provide close tolerances therebetween whereby with the head 39 in place the joint will be firm and without looseness but wherein it can still pivot easily and smoothly. The limits of said pivoting are determined by the surfaces 10 and 11 as will be apparent from FIG. 2.

OPERATION

It will be apparent from the drawings that the parts are assembled by placing the head 39 against hemicylindrical surface of the recess 9 and moving same axially until the rightward (as seen in FIG. 1) end 39A of said head enters fully into the blind opening 12. This brings the end 39B of said cylinder substantially flush with the end surface 23 of the recess part 1. The end cap 6 is then put in place with its projecting portion 31 located between said head 39 and the platform 34. The screws 18 are put into place through the openings 13 and then into the openings 16 and suitably tightened. The head 39 is thus firmly captured within the recess provided by the recess part 1 and only under exceptional conditions will any axial stress be applied to the screws 18. When the user is standing, the load is connected directly from the recess portion 1 through the surface 32 thereof against the surface 36 and to the prong 4. If there is simultaneous contact between the upper end of the head 39 and the surface cooperating therewith of the hemispherical recess 9, the plastic parts have sufficient resilience to permit the pressure to become substantially equalized between said parts and the surfaces 32 and 36. Likewise under such conditions, the entire length of the head 39 bears against the single molding comprising the recess part 1 and no pressure at all is applied to any part of the screws 18.

With the user in a crouched or sitting position, the load is similarly transmitted from the recess portion 1 to the cylinder portion 3 and no stress whatever is placed upon said screws.

When, however, the user's foot is lifted so that tension force is placed upon his leg, then a portion of such load is placed upon the flange 41 of the end portion 8 which it will be noted is molded as an integral part of the recess portion 1 and only a portion of such tension load is placed upon the flange 31 of the end cap 6. Even this, however, is applied through the screws 18 as shear stress and will be adequately held by even relatively small screws.

The only way in which an axial stress may be applied to said screws is when there is a side thrust placed upon one portion of the user's leg which is resisted by the other portion thereof and this will be of only minor magnitudes in all normal situations.

Accordingly, the objects of the invention as above set forth are adequately accomplished by the prosthesis as above described and illustrated by the accompanying drawings and the loading on the prosthesis under any normal use will seldom, if ever, exceed 300 psi.

Although a particular preferred embodiment of the invention has been disclosed in detail for illustrative purposes, it will be recognized that variations or modifications of the disclosed apparatus, including the rearrangement of parts, lie within the scope of the present invention.

The embodiments of the invention in which an exclusive property of privilege is claimed are defined as follows:

1. In a prosthetic knee joint, the combination comprising:
    a recess portion having a prong and a head on an end thereof, said head comprising a central portion having a centrally located partially cylindrical surface defining a recess and further comprising an end portion defining a first blind opening including a surface comprising a continuation of said partially cylindrical surface, said partially cylindrical surface being limited at each end thereof by limit surfaces spaced from each other and extending from said partially cylindrical surface to points on the outer peripheral surface of said head to determine the limits of pivotal movement of said knee joint;

a cap portion bearing against the end of said central portion opposite said end portion and defining with said central portion a second blind opening concentric with and identical in mirror image with said first blind opening, said first blind opening, said partially cylindrical surface and said second blind opening all being coaxial with respect to each other on a central axis and the surface of contact between said cap portion and the adjacent end of said central portion being perpendicular to the said central axis;

removable means for fixing said cap portion rigidly to said central portion;

a cylinder part snugly but pivotally received within said recess and having a neck extending generally radially outwardly therefrom between said limit surfaces;

a platform at the end of said neck arranged generally perpendicular to the direction of such extent and a prong projecting beyond said platform in the direction comprising substantially a continuation of the direction of projection of said neck.

2. The joint of claim 1 wherein the outer peripheral surface of said head in the region generally from a zone of one limit surface to a zone of the other limit surface is cylindrically arcuate and concentric with said central axis wherein the surface of said platform opposed thereto is likewise cylindrically arcuate and similarly concentric and wherein the dimensioning of said components provides that when said cylinder part is operatively received within said recess, said two last-named cylindrically arcuate surfaces will be in load bearing contact with each other.

3. The joint of claim 1 wherein the depth of the first blind opening and the length of the partially cylindrical surface adjacent thereto are together at least as long as the axial length of said cylinder part, whereby the entire load imposed on said prosthesis in a direction generally axially of said prongs is transmitted between said recess portion and said cylinder part.

4. The joint of claim 1 wherein the depth of the first blind opening and the length of the partially cylindrical surface adjacent thereto are together equal to the axial length of said cylinder, whereby the entire load imposed on said prosthesis in a direction generally axially of said prongs is transmitted between said recess portion and said cylinder part.

5. The joint of claim 1 including also a slide for insertion between the natural knee cap and the prosthetic joint, said slide including means for fixing same firmly to said knee cap and shaped to slide smoothly against the surface of said prosthetic joint opposed thereto.

* * * * *